(12) United States Patent  
Zhang et al.

(10) Patent No.: US 8,189,893 B2
(45) Date of Patent: May 29, 2012

(54) METHODS, SYSTEMS, AND COMPUTER PROGRAM PRODUCTS FOR BINARY MULTIPLEXING X-RAY RADIOGRAPHY

(75) Inventors: Jian Zhang, Chapel Hill, NC (US); Jianping Lu, Chapel Hill, NC (US); Otto Z. Zhou, Chapel Hill, NC (US); David Lalush, Cary, NC (US)

(73) Assignees: The University of North Carolina at Chapel Hill, Chapel Hill, NC (US); North Carolina State University, Raleigh, NC (US)

( * ) Notice: Subject to any disclaimer, the term of this patent is extended or adjusted under 35 U.S.C. 154(b) by 1059 days.

(21) Appl. No.: 11/804,897

(22) Filed: May 21, 2007

(65) Prior Publication Data

US 2008/0069420 A1 Mar. 20, 2008

Related U.S. Application Data

(60) Provisional application No. 60/802,260, filed on May 19, 2006.

(51) Int. Cl.
*G06K 9/00* (2006.01)
*H05G 1/60* (2006.01)

(52) U.S. Cl. ............... 382/131; 382/132; 378/9; 378/16

(58) Field of Classification Search .................. 382/131, 382/132; 378/4, 9, 12, 16
See application file for complete search history.

(56) References Cited

U.S. PATENT DOCUMENTS

| | | | |
|---|---|---|---|
| 2,842,706 A | 7/1958 | Dobischek et al. | |
| 3,617,285 A | 11/1971 | Staudenmayer | |
| 3,733,484 A | 5/1973 | Bayard | |
| 3,753,020 A | 8/1973 | Zingaro | |
| 3,783,288 A | 1/1974 | Barbour et al. | |
| 3,921,022 A | 11/1975 | Levine | |
| 3,932,756 A | 1/1976 | Cowell et al. | |
| 4,012,656 A | 3/1977 | Norman et al. | |
| 4,253,221 A | 3/1981 | Cochran, Jr. et al. | |
| 4,289,969 A | 9/1981 | Cooperstein et al. | |
| 4,382,184 A | 5/1983 | Wernikoff | |
| 4,712,226 A | 12/1987 | Horbaschek | |

(Continued)

FOREIGN PATENT DOCUMENTS

CN 2336381 Y 9/1999

(Continued)

OTHER PUBLICATIONS

Bentley, M.D. et al., "The Use of Microcomputed Tomography to Study Microvasculature in Small Rodents", *Am. J Physiol Regulatory Integrative Comp Physiol*, 282, pp. R1267-1279, 2002.

(Continued)

*Primary Examiner* — Jon Chang

(74) *Attorney, Agent, or Firm* — Jenkins, Wilson, Taylor & Hunt, P.A.

(57) ABSTRACT

Methods, systems, and computer program products for binary multiplexing x-ray radiography are disclosed. According to one aspect, the subject matter described herein can include irradiating an object with composite x-ray beams including signals based on a predetermined binary transform. Further, the subject matter described herein can include detecting x-ray intensities associated with the signals of the composite x-ray beams. An inverse binary transform can be applied to the detected x-ray intensities associated with the signals of the composite x-ray beams to recover the signals of the composite x-ray beams.

24 Claims, 9 Drawing Sheets

U.S. PATENT DOCUMENTS

| | | | |
|---|---|---|---|
| 4,780,612 A | 10/1988 | Klatt | |
| 4,809,308 A | 2/1989 | Adams et al. | |
| 4,926,452 A | 5/1990 | Baker et al. | |
| 4,958,365 A | 9/1990 | Sohval et al. | |
| 5,129,850 A | 7/1992 | Kane et al. | |
| 5,138,237 A | 8/1992 | Kane et al. | |
| 5,245,648 A | 9/1993 | Kinney et al. | |
| 5,305,363 A | 4/1994 | Burke et al. | |
| 5,371,778 A | 12/1994 | Yanof et al. | |
| 5,377,249 A | 12/1994 | Wiesent et al. | |
| 5,390,112 A | 2/1995 | Tam | |
| 5,412,703 A | 5/1995 | Goodenough et al. | |
| 5,424,054 A | 6/1995 | Bethune et al. | |
| 5,557,105 A | 9/1996 | Honjo et al. | |
| 5,578,821 A | 11/1996 | Meisberger et al. | |
| 5,594,770 A | 1/1997 | Bowles et al. | |
| 5,616,368 A | 4/1997 | Jin et al. | |
| 5,623,180 A | 4/1997 | Jin et al. | |
| 5,637,950 A | 6/1997 | Jin et al. | |
| 5,648,699 A | 7/1997 | Jin et al. | |
| 5,692,028 A | 11/1997 | Geus et al. | |
| 5,726,524 A | 3/1998 | Debe | |
| 5,745,437 A | 4/1998 | Wachter et al. | |
| 5,764,683 A | 6/1998 | Swift et al. | |
| 5,773,834 A | 6/1998 | Yamamoto et al. | |
| 5,773,921 A | 6/1998 | Keesmann et al. | |
| 5,834,783 A | 11/1998 | Muraki et al. | |
| 5,844,963 A | 12/1998 | Koller et al. | |
| 5,910,974 A | 6/1999 | Kuhn et al. | |
| 5,973,444 A | 10/1999 | Xu et al. | |
| RE36,415 E | 11/1999 | McKenna | |
| 5,976,444 A | 11/1999 | Pearson et al. | |
| 6,019,656 A | 2/2000 | Park et al. | |
| 6,028,911 A | 2/2000 | Kawahara | |
| 6,057,637 A | 5/2000 | Zettl et al. | |
| 6,087,765 A | 7/2000 | Coll et al. | |
| 6,097,138 A | 8/2000 | Nakamoto | |
| 6,097,788 A | 8/2000 | Berenstein et al. | |
| 6,125,167 A | 9/2000 | Morgan | |
| 6,178,226 B1 | 1/2001 | Hell et al. | |
| 6,192,104 B1 | 2/2001 | Adams et al. | |
| 6,250,984 B1 | 6/2001 | Jin et al. | |
| 6,259,765 B1 | 7/2001 | Baptist | |
| 6,271,923 B1 | 8/2001 | Hill | |
| 6,277,318 B1 | 8/2001 | Bower et al. | |
| 6,280,697 B1 | 8/2001 | Zhou et al. | |
| 6,297,592 B1 | 10/2001 | Goren et al. | |
| 6,333,968 B1 | 12/2001 | Whitlock et al. | |
| 6,334,939 B1 | 1/2002 | Zhou et al. | |
| 6,350,628 B1 | 2/2002 | Cheng et al. | |
| 6,376,973 B1 | 4/2002 | Blanchet-Fincher et al. | |
| 6,385,292 B1 | 5/2002 | Dunham et al. | |
| 6,440,761 B1 | 8/2002 | Choi | |
| 6,445,122 B1 | 9/2002 | Chuang et al. | |
| 6,456,691 B2 | 9/2002 | Takahashi et al. | |
| 6,459,767 B1 | 10/2002 | Boyer et al. | |
| 6,470,068 B2 | 10/2002 | Cheng | |
| 6,498,349 B1 | 12/2002 | Thomas et al. | |
| 6,510,195 B1 | 1/2003 | Chappo et al. | |
| 6,529,575 B1 | 3/2003 | Hsieh | |
| 6,545,396 B1 | 4/2003 | Ohki et al. | |
| 6,553,096 B1 | 4/2003 | Zhou et al. | |
| 6,560,309 B1 | 5/2003 | Becker et al. | |
| RE38,223 E | 8/2003 | Keesmann et al. | |
| 6,621,887 B2 | 9/2003 | Albagli et al. | |
| 6,630,772 B1 | 10/2003 | Bower et al. | |
| 6,650,730 B2 | 11/2003 | Bogatu et al. | |
| 6,672,926 B2 | 1/2004 | Liu et al. | |
| 6,674,837 B1 | 1/2004 | Taskar et al. | |
| 6,754,300 B2 | 6/2004 | Hsieh et al. | |
| 6,760,407 B2 | 7/2004 | Price et al. | |
| RE38,561 E | 8/2004 | Keesmann et al. | |
| 6,787,122 B2 | 9/2004 | Zhou | |
| 6,850,595 B2 | 2/2005 | Zhou et al. | |
| 6,852,973 B2 | 2/2005 | Suzuki et al. | |
| 6,876,724 B2 | 4/2005 | Zhou et al. | |
| 6,950,493 B2 * | 9/2005 | Besson | 378/16 |
| 6,965,199 B2 | 11/2005 | Stoner et al. | |
| 6,980,627 B2 | 12/2005 | Qiu et al. | |
| 7,027,558 B2 | 4/2006 | Ghelmansarai et al. | |
| 7,046,757 B1 | 5/2006 | Bani-Hashemi et al. | |
| 7,082,182 B2 | 7/2006 | Zhou et al. | |
| 7,085,351 B2 | 8/2006 | Lu et al. | |
| 7,147,894 B2 | 12/2006 | Zhou et al. | |
| 7,220,971 B1 | 5/2007 | Chang et al. | |
| 7,227,924 B2 | 6/2007 | Zhou et al. | |
| 7,245,692 B2 | 7/2007 | Lu et al. | |
| 7,359,484 B2 | 4/2008 | Qiu et al. | |
| 7,420,174 B2 | 9/2008 | Kurita et al. | |
| 7,741,624 B1 | 6/2010 | Sahadevan | |
| 7,751,528 B2 | 7/2010 | Zhou et al. | |
| 7,835,492 B1 | 11/2010 | Sahadevan | |
| 7,902,530 B1 | 3/2011 | Sahadevan | |
| 2001/0019601 A1 | 9/2001 | Tkahashi et al. | |
| 2002/0085674 A1 | 7/2002 | Price et al. | |
| 2002/0094064 A1 | 7/2002 | Zhou et al. | |
| 2002/0110996 A1 | 8/2002 | Yaniv et al. | |
| 2002/0140336 A1 | 10/2002 | Stoner et al. | |
| 2002/0159565 A1 * | 10/2002 | Muller et al. | 378/98.12 |
| 2002/0171357 A1 | 11/2002 | Sun et al. | |
| 2002/0191751 A1 | 12/2002 | Bogatu et al. | |
| 2002/0193040 A1 | 12/2002 | Zhou | |
| 2003/0002627 A1 | 1/2003 | Espinosa et al. | |
| 2003/0002628 A1 | 1/2003 | Wilson et al. | |
| 2003/0048868 A1 | 3/2003 | Bailey et al. | |
| 2003/0102222 A1 | 6/2003 | Zhou et al. | |
| 2003/0103666 A1 * | 6/2003 | Edic et al. | 382/132 |
| 2003/0142790 A1 | 7/2003 | Zhou et al. | |
| 2003/0198318 A1 | 10/2003 | Price et al. | |
| 2004/0017888 A1 | 1/2004 | Seppi et al. | |
| 2004/0036402 A1 | 2/2004 | Keesmann et al. | |
| 2004/0065465 A1 | 4/2004 | Chappo et al. | |
| 2004/0108298 A1 | 6/2004 | Gao | |
| 2004/0114721 A1 | 6/2004 | Qiu et al. | |
| 2004/0213378 A1 | 10/2004 | Zhou et al. | |
| 2004/0240616 A1 | 12/2004 | Qiu et al. | |
| 2004/0256975 A1 | 12/2004 | Gao et al. | |
| 2005/0028554 A1 | 2/2005 | Wanner et al. | |
| 2005/0084073 A1 | 4/2005 | Seppi et al. | |
| 2005/0117701 A1 * | 6/2005 | Nelson et al. | 378/87 |
| 2005/0133372 A1 | 6/2005 | Zhou et al. | |
| 2005/0175151 A1 | 8/2005 | Dunham et al. | |
| 2005/0226361 A1 | 10/2005 | Zhou et al. | |
| 2005/0226371 A1 | 10/2005 | Kantzer et al. | |
| 2005/0269559 A1 | 12/2005 | Zhou et al. | |
| 2006/0018432 A1 | 1/2006 | Zhou et al. | |
| 2006/0291711 A1 * | 12/2006 | Jabri et al. | 382/132 |
| 2007/0009081 A1 | 1/2007 | Zhou et al. | |
| 2008/0031400 A1 * | 2/2008 | Beaulieu et al. | 378/4 |
| 2010/0239064 A1 | 9/2010 | Zhou et al. | |
| 2010/0329413 A1 | 12/2010 | Zhou et al. | |

FOREIGN PATENT DOCUMENTS

| | | |
|---|---|---|
| CN | ZL200680013859.X | 1/2011 |
| DE | 197 00 992 | 7/1998 |
| DE | 101 64 315 A1 | 8/2002 |
| DE | 101 64 318 A1 | 8/2002 |
| EP | 0 268 488 | 5/1988 |
| EP | 1 050 272 A1 | 11/2000 |
| EP | 0 648 468 | 4/2005 |
| GB | 679617 | 9/1952 |
| JP | 53103392 A | 9/1978 |
| JP | A S54-027793 | 3/1979 |
| JP | 57162431 A2 | 10/1982 |
| JP | 60254615 A2 | 12/1985 |
| JP | A S61-142644 | 6/1986 |
| JP | 06163381 A2 | 6/1994 |
| JP | 09180894 A | 7/1997 |
| JP | A H09-180894 | 7/1997 |
| JP | 2000251826 A2 | 2/1999 |
| JP | 11-111158 | 4/1999 |
| JP | A H11-116218 | 4/1999 |
| JP | 11-260244 | 9/1999 |
| JP | 08264139 A | 10/1999 |
| JP | 2000208028 | 7/2000 |
| JP | A 2001-048509 | 2/2001 |
| JP | 2001190550 A | 7/2001 |

| JP | A 2001250496 A | 9/2001 |
| --- | --- | --- |
| JP | 2003100242 A | 4/2003 |
| JP | 2003100242 A | 4/2003 |
| TW | 00319886 | 11/1997 |
| TW | 0379354 B | 1/2000 |
| TW | 0439303 B | 6/2001 |
| TW | 0527624 B | 4/2003 |
| TW | 0529050 B | 4/2003 |
| WO | WO 00/51936 A3 | 9/2000 |
| WO | WO 02/03413 | 1/2002 |
| WO | WO 02/31857 | 4/2002 |
| WO | WO 03/012816 A2 | 2/2003 |
| WO | WO 2004/061477 | 7/2004 |
| WO | WO 2004/096050 | 11/2004 |
| WO | WO 2004097889 A2 * | 11/2004 |
| WO | WO 2005/079246 | 1/2005 |

OTHER PUBLICATIONS

Bonard et al., "Field emission from single-wall carbon nanotube films", *Appl. Phys. Left.*, vol. 73, No. 7, pp. 918-920 (Aug. 17, 1998).
Bower et al., "Synthesis and structure of pristine and alkali-metal-intercalated single-walled carbon nanotubes", *Appl. Phys.*, A 67, pp. 47-52 (1998).
Bower, C. et al., "Fabrication and Field Emission Properties of Carbon Nanotube Cathodes", *Mat. Res. Soc. Symp. Proc.*, vol. 593, pp. 215-220, 2000.
Brock et al., "Hadamard Transform Time-of-Flight Mass Spectrometry," Analytical Chemistry, vol. 70, No. 18, Sep. 15, 1998.
Brodie et al., "Vacuum Microelectronics", *Advance in Electronics and Electron Physics*, edited by P.W. Hawkes, vol. 83, pp. 1-106 (1992).
Bushong, S.C., "Radiologic Science for Technologist," Physics, Biology, and Protection, 6$^{th}$ Edition, Mosby, Inc., 1997 (excerpt relating to focusing and thermionic emission).
Cassell et al., "Large Scale CVD Synthesis of Single-Walled Carbon Nanotubes", *J. Phys. Chem.*, B 103, pp. 6484-6492 (Jul. 20, 1999).
Charbonnier et al., "Resolution of Field-Emmision X-Ray Sources," *Radiology*, vol. 117: pp. 165-172 (Oct. 1975).
Cheng et al., "Dynamic radiography using a carbon-nanotube-based field emission x-ray source," *Review of Scientific Instruments*, vol. 75, No. 10: pp. 3264-3267 (Oct. 2004).
Cheng et al., "Electron Field Emission from Carbon Nanotubes," *C.R. Physique*, pp. 1021-1033 (2003).
de Heer et al., "A Carbon Nanotube Field-Emission Electron Source", *Science*, vol. 270, pp. 1179-1180 (Nov. 17, 1995).
Dobbins III et al., "Digital x-ray tomosynthesis: current state of the art and clinical potential," *Phys. Med. Biol.* 48 (2003) R65-R106.
Feldkamp L.A. et al., "Practical Cone-Beam Algorithm", *J. Opt. Soc. Am.*, 1(a):612-619, 1984.
Gao et al., "Fabrication and Electron Field Emmision Properties of Carbon Nanotube Films by Electrophoretic Deposition," *Advanced Materials*, vol. 13, No. 23 (2001).
Geis et al., "Diamond emitters fabrication and theory", *J. Vac. Sci. Technol. B*, vol. 14, No. 3, pp. 2060-2067, May/Jun. 1996.
Hallenbeck, "Clinical Evaluation of the 350-kV Chest Radiography System," *Radiology*, vol. 117: pp. 1-4 (1974).
Hu, J. et al., "Chemistry and Physics in One Dimension: Synthesis and Properties of Nanowires and Nanotubes", *Accounts of Chemical Research*, vol. 32, pp. 435-445, 1999.
Jerri, "The Shannon Sampling Theorem—Its Various Extensions and Applications: A Tutorial Review," *IEEE*, vol. 65, No. 11, pp. 1565-1596 (1977).
Journet et al., "Large-scale production of single-walled carbon nanotubes by the electric-arc technique", *Nature*, vol. 388, pp. 756-760 (Aug. 21, 1997).
Kruger et al., "Tomosynthesis Applied to Digital Subtraction Angiography," *Radiology*, V152, pp. 805-808 (1984).
Kumar et al., "Diamond-based field emission flat panel displays", *Solid State Technology*, vol. 38, pp. 71-74 (May 1995).
Lalush, "Feasibility of Transmission Micro-CT with Two Fan-Beam Sources," *Proceedings of 26$^{th}$ Annual Int'l Conf on IEEE EMBS*, pp. 1283-1286, Sep. 5, 2004.
Lee et al., "Novel Micro-CT Based on a Carbon Nanotube Field Emission X-ray Source," *2003 Radiological Society of North American Meeting*, Abstract Code A21-182, Nov. 30, 2003.
Moore et al., "Three-Dimensional X-Ray Laminography as a Tool for Detection and Characterization of BGA Package Defects", IEEE Transactions on Components and Packaging Technologies. vol. 25, No. 2, Jun. 2002.
Nyquist, "Certain Topics in Telegraphic Transmission Theory," *IEEE*, vol. 2, No. 2, pp. 208-305 (2002).
Okano et al., "Electron emission from nitrogen-doped pyramidal-shape diamond and its battery operation", *Appl. Phys. Lett.*, vol. 70, No. 16, pp. 2201-2203 (Apr. 21, 1997).
Okano et al., "Fabrication of a diamond field emitter array", *Appl. Phys. Lett.*, vol. 64, No. 20, pp. 2742-2744 (May 16, 1994).
Okazaki et al., "A New Emission Spectrum of $Au^2$ in the Gas Evaporation Technique: 761-809 nm", *Jpn. J. Appl. Phys.*, vol. 37, Pt. 1, No. 1, pp. 349-350 (Jan. 1998).
Resat et al., "Microbeam developments and applications: A low linear energy transfer perspective," Cancer and Metastasis Reviews 23: p. 323-331 (2004).
Ribbing et al., "Diamond membrane based sructures for miniature X-ray sources," Diamond and Related Materials, vol. 11: pp. 1-7 (2002).
Rinzler et al., "Unraveling Nanotubes: Field Emission from an Atomic Wire", *Science*, vol. 269, pp. 1550-1553 (Sep. 15, 1995).
Saito, Y. et al., "Field Emission Patterns from Single-Walled Carbon Nanotubes", *Jpn. J. Appl. Phys.*, vol. 36, pp. L1340-L1342, Part 2, No. 10A, Oct. 1, 1997.
Saito, Y. et al., "Cathode Ray Tube Lighting Elements with Carbon Nanotube Field Emitters", *Jpn. J. Appl. Phys.*, vol. 37, pp. L346-L348. Part 2, No. 3B, Mar. 15, 1998.
Shannon, "Communication in the Presence of Noise," *IEEE*, vol. 86, No. 2, pp. 447-108(1998).
Sloane, "Multiplexing Methods in Spectroscopy," Mathematics Magazine, vol. 52, No. 2 (Mar. 1979), 71-80.
Sugie et al., "Carbon nanotubes as electron source in an x-ray tube," Applied Physics Letters, vol. 78, No. 17: pp. 2578-2580 (2001).
Tang, X. P. et al., "Electronic Structures of Single-Walled Carbon Nanotubes Determined by NMR", *Science*, vol. 288, pp. 492-494 (Apr. 21, 2000).
Thess, A. et al., "Crystalline Ropes of Metallic Carbon Nanotubes", *Science*, vol. 273, pp. 483-487 (Jul. 26, 1996).
Traedo, "A Thousand Points of Light: The Hadamard Transform in Chemical Analysis and Instrumentation," Analytical Chemistry. vol. 61, No. 11, Jun. 1, 1989.
Vogel et al., "A New Method of Multiplanar Emission Tomography Using a Seven Pinhole Collimator and an Anger Scintillation Camera," *Jour. Nuclear Medicine*, vol. 19, No. 6, pp. 648-654, 1978.
Wang et al., "Field Emission From Nanotube Bundle Emitters at Low Fields", *App. Phys. Lett.*, 70(24), pp. 3308-3310, Jun. 16, 1997.
Wang et al., "A nanotube-based field-emission flat panel display", *Appl. Phys. Lett.*, vol. 72, No. 2, pp. 2912-2913 (Jun. 1, 1998).
Weinstein et al., "Data Transmission by Frequency-Division Multiplexing Using the Discrete Fourier Transform," IEEE Trans. on Commun. Tech., vol. Com-19, No. 5, pp. 628-634, Oct. 1971.
Weisstein, "CRC Concise Encyclopedia of Mathematics," Second Ed., pp. 1, 54, 1092-1097, 1936, 2046 and 2615 (2003).
Yagishita et al., "Effects of Cleavage on Local Cross-Sectional Stress Distribution in Trench Isolation Structure", *Jpn. J. Appl. Phys.*, vol. 36, pp. 1335-1340 (Mar. 1997).
Yue et al., "Generation of continuous and pulsed diagnostic imaging x-ray radiation using a carbon nontube based field emission cathode," Applied Physics Letters, vol. 81, No. 2: pp. 355-357 (F) Jul. 8, 2002.
Zhang et al., "Multiplexing radiography using a carbon nanotube based x-ray source," Applied Physics Letters, vol. 89, 2006.
Zhang et al., "Stationary scanning x-ray source based on carbon nanotube field emitters," Applied Physics Letters, vol. 86, 2005.
Zhou et al., "Materials Science of Carbon Nanotubes: Fabrication, Integration, and Properties of Macroscopic Structures of Carbon Nanotubes", *Acc. Chem. Res.*, vol. 35, pp. 1045-1053, 2002.
Zhu et al., "Low-Field Electron Emission from Updoped Nanostructured Diamond", *Science*, vol. 282, 1471-1473 (Nov. 20, 1998).

Zhu, W. et al., "Large Current Density from Carbon Nanotube Filed Emitters", *Appl. Phys. Lett.*, American Institute of Physics, vol. 75, No. 6, Aug. 9, 1999, pp. 873-875.
Non-final Office Action for U.S. Appl. No. 09/679,303 dated Jan. 16, 2002.
Final Office Action for U.S. Appl. No. 09/679,303 dated May 6, 2002.
Non-final Office Action for U.S. Appl. No. 09/679,303 dated Aug. 20, 2002.
Notice of Allowance for U.S. Appl. No. 09/679,303 dated Nov. 1, 2002.
Office Communication for U.S. Appl. No. 09/679,303 dated Feb. 6, 2003.
International Search Report for Application No. PCT/US03/00537 dated Apr. 10, 2003.
Non-final Office Action for U.S. Appl. No. 10/309,126 dated May 22, 2003.
Non-final Office Action for U.S. Appl. No. 10/051,183 dated Sep. 10, 2003.
Non-final Office Action for U.S. Appl. No. 10/309,126 dated Nov. 5, 2003.
Non-final Office Action for U.S. Appl. No. 10/309,126 dated Apr. 20, 2004.
Non-final Office Action for U.S. Appl. No. 10/051,183 dated Apr. 21, 2004.
Notice of Allowance for U.S. Appl. No. 10/309,126 dated Aug. 26, 2004.
Notice of Allowance for U.S. Appl. No. 10/051,183 dated Aug. 31, 2004.
Corrected Notice of Allowance for U.S. Appl. No. 10/309,126 dated Sep. 14, 2004.
Non-final Office Action for U.S. Appl. No. 10/358,160 dated Sep. 21, 2004.
Office Communication for U.S. Appl. No. 10/051,183 dated Jan. 14, 2005.
International Search Report and Written Opinion for PCT/US04/12660 dated Apr. 7, 2005.
Non-final Office Action U.S. Appl. No. 10/358,160 dated Jun. 7, 2005.
Office Action-Restriction requirement U.S. Appl. No. 10/358,160 dated Oct. 26, 2005.
Notice of Allowance U.S. Appl. No. 10/358,160 dated Feb. 8, 2006.
International Search Report and Written Opinion for Application No. PCT/US05/03991 dated Jun. 22, 2006 / Aug. 14, 2006.
Non-Final Office Action for U.S. Appl. No. 11/320,515 dated Aug. 17, 2006.
Office Action-Restriction requirement for U.S. Appl. No. 11/051,332 dated Sep. 7, 2006.
International Search Report for corresponding International Application No. PCT/US05/47066 dated Oct. 6, 2006.
Notice of Allowance dated for U.S. Appl. No. 11/051,332 dated Dec. 28, 2006.
International Preliminary Report on Patentability for PCT/US04/12660 dated May 9, 2007.
International Search Report for PCT/US06/37046 dated May 21, 2007.
Korean Intellectual Property Office (KIPO) Office Action for Korean Patent Application No. 10-2004-7011373 dated Jun. 11, 2007.
European Patent Office Examination Report dated Jun. 28, 2007 for European Patent Application No. 03702044.3.
Korean Intellectual Property Office (KIPO) Office Action for Korean Patent Application No. 10-2003-700004987 dated Jul. 19, 2007.
Second Chinese Office Action for Patent Application No. 03806739.0 dated Oct. 19, 2007.
Non-final Office Action for U.S. Appl. No. 11/415,953 dated Dec. 11, 2007.
Korean Office Action for Korean Patent Application No. 10-2004-7011373 dated Dec. 18, 2007.
Taiwanese Office Action for Taiwan Patent No. 093102622 dated Dec. 21, 2007.
Examination Report from European Patent Office dated Mar. 3, 2008 for European Patent Application No. 03702044.3.
Third Chinese Office Action dated Mar. 14, 2008 for Chinese Patent Application No. 01820211.X (PCT/US01/30027).
Non-final Office Action for U.S. Appl. No. 10/970,384 dated Apr. 8, 2008.
Office Action-Restriction requirement for U.S. Appl. No. 11/415,953 dated May 22, 2008.
Office Action from Canadian Patent Office dated May 27, 2008 for Canadian Application No. 2,424,826.
Japanese Patent Office Action for JP No. 2003-562962 for corresponding PCT No. US03/00537 dated Jun. 20, 2008.
Office Action from Japanese Patent Office for Japanese Patent Application No. 2003-580561 for corresponding PCT No. US03/06345 dated Sep. 3, 2008.
International Search Report and Written Opinion for PCT Application No. PCT/US08/70477 dated Oct. 1, 2008.
First Office Action from Japanese Patent Office for Japanese Patent Application No. 2002-535152, based on PCT/US01/30027 dated Oct. 17, 2008.
First Office Action from Japanese Patent Office dated Jan. 6, 2009 for JP Application No. 2006-513282.
Notice of Publication for Chinese Patent Application No. 200810215733.1 (Publication No. 101352353) dated Jan. 28, 2009.
Confirmation of issuance of Chinese Patent No. ZL01820211.X corresponding to PCT/US01/30027 dated Feb. 4, 2009.
Confirmation that Chinese Application 093102622 issued on Mar. 1, 2009 as Patent No. TW I307110.
First Office Action from Chinese Patent Office dated Mar. 6, 2009 for Chinese Patent Application No. 200480017120.7.
Japanese Final Office Action for Japanese Patent Application No. 2003-562962 based on PCT/US03/00537 dated Mar. 30, 2009.
First Office Action from Chinese Patent Office for Chinese Patent Application No. 200710003710.X dated Apr. 24, 2009.
Office Action-Final for U.S. Appl. No. 11/441,281 dated Jun. 4, 2009.
Supplementary European Search Report for European Patent Application No. 01981327.8 dated Jun. 22, 2009.
Non-Final Office Action for U.S. Appl. No. 12/176,056 dated Sep. 2, 2009.
First Office Action from Chinese Patent Office for Chinese Patent Application Serial No. 200680013859.X dated Sep. 25, 2009.
Supplementary European Search report dated Oct. 7, 2009 for EPO Application No. 04 77 5902 (PCT/US2004012660).
Second Office Action from Japanese Patent Office dated Dec. 7, 2009 for Japanese Patent Application No. 2002-535152.
Decision on Rejection issued from the Chinese Patent Office dated Dec. 11, 2009 for Chinese Application No. 200710003710.X.
Non-final Office Action for U.S. Appl. No. 11/441,281 dated Jan. 11, 2010.
Second Office Action corresponding to Chinese Patent Application No. 200680013859 dated Apr. 30, 2010.
First Office Action corresponding to Chinese Patent Application No. 200680043786.9 dated Jul. 6, 2010.
Final Office Action for U.S. Appl. No. 11/441,281 dated Sep. 30, 2010.
Non-Final Office Action for U.S. Appl. No. 11/526,217 dated Oct. 13, 2010.
Second Office Action for CN Appl. No. 2004-80017120.7 dated Nov. 17, 2010.
Third Office Action for CN Appl. No. 2008-10215733.1 dated Dec. 14, 2010.
Non-Final Office Action for U.S. Appl. No. 11/441,281 dated Mar. 15, 2011.
Lee et al., "Pulsed X-Ray Imaging of Small Animals Using a Carbon Nanotube Based X-Ray Source" presented at the Academy of Molecular Imaging Annual Meeting, Orlando, FL, Mar. 2004, Molecular Imaging and Biology, vol. 6, No. 2, Abstract No. 41, p. 80.
U.S. Appl. No. 12/655,825, filed Jan. 7, 2010 entitled "System and Method for All Field Simultaneous Radiation Therapy and Concealed Object Screening . . . ".
Third-Party Submission against U.S. Appl. No. 12/688,425 dated Feb. 28, 2011.
Second Office Action for CN Appl. No. 2006-80043786.9 dated Mar. 2, 2011.
Final Office Action for U.S. Appl. No. 11/526,217 dated May 6, 2011.
First Office Action for CN Appl. No. 200880107680.X dated Apr. 7, 2011.

Notification to Grant for Chinese Patent Application No. 200810215733.1 dated Jun. 2, 2011.
Notification to Grant for Chinese Patent Application No. 200480017120.7 dated Jul. 12, 2011.
Final Office Action for U.S. Appl. No. 11/526,217 dated Aug. 19, 2011.
Japanese Office Action for JP Appl. No. 2008-532428 dated Sep. 20, 2011.
Non-Final Office Action for U.S. Appl. No. 11/441,281 dated Oct. 19, 2011.

* cited by examiner

HADAMARD ENCODING $$\begin{pmatrix} Y_1 \\ Y_2 \\ Y_3 \end{pmatrix} = \begin{pmatrix} 1 & 1 & 0 \\ 1 & 0 & 1 \\ 0 & 1 & 1 \end{pmatrix} \begin{pmatrix} X_1 \\ X_2 \\ X_3 \end{pmatrix} \Leftrightarrow \begin{pmatrix} X_1 \\ X_2 \\ X_3 \end{pmatrix} = \frac{1}{2} \begin{pmatrix} 1 & 1 & -1 \\ 1 & -1 & 1 \\ -1 & 1 & 1 \end{pmatrix} \begin{pmatrix} Y_1 \\ Y_2 \\ Y_3 \end{pmatrix}$$

$\otimes\ S^{-1}$ ⇒

METHODS, SYSTEMS, AND COMPUTER PROGRAM PRODUCTS FOR BINARY MULTIPLEXING X-RAY RADIOGRAPHY

RELATED APPLICATION

The presently disclosed subject matter claims the benefit of U.S. Provisional Patent Application Ser. No. 60/802,260, filed May 19, 2006, the disclosure of which is incorporated herein by reference in its entirety.

GOVERNMENT INTEREST

This work was supported at least in part by a grant from the National Institute of Health and the National Institute of Biomedical Imaging and Bioengineering (NIH-NIBIB) (Grant No. 4-R33-EB004204-02), and a grant from the National Cancer Institute (NCI) (Grant No. U54CA119343). Thus, the U.S. Government may have certain rights in the presently disclosed subject matter.

TECHNICAL FIELD

The subject matter described herein relates to x-ray radiography. More specifically, the subject matter describes methods, systems, and computer program products for binary multiplexing x-ray radiography.

BACKGROUND

X-ray radiation is widely used in many areas including medical diagnostics and treatment, industrial inspection and testing, security screening and detections. Current x-ray sources are mostly based on a thermionic cathode to generate electron beam, which is accelerated to high energy to bombard a metal target to generate x-ray. Thermionic cathode based x-ray sources cannot be easily switched on/off rapidly and the x-ray flux cannot be easily controlled due to the slow response of thermal process and the nonlinear relationship between the cathode current and the electron beam current. At the same time, the hot filament based x-ray tube is generally bulky due to the heating and insulation parts required for the filament heating. It is in principle difficult to integrate multiple x-ray units together to form an integrated multi-beam x-ray source which can provide multiple x-ray beams simultaneously.

Recently, x-ray generating devices and methods based on nanostructure containing field emission cathodes have been developed. Examples of such x-ray generating devices and methods are described in U.S. Pat. Nos. 6,553,096, 6,850,595, and 6,876,724. These devices and methods provide several advantages over conventional hot filament based x-ray tubes. Firstly, the field emission x-ray (FEX) source can be easily triggered to generate x-ray pulse in arbitrary temporal waveform. This feature can enable new radiography imaging techniques that are not possible (or practical) with conventional x-ray sources. Secondly, the field emission x-ray source operates at room temperature, which is much lower than conventional hot filament based x-ray tubes. Further, because there is no heat, it is free of bulky insulation or ventilation components, so such a device is much smaller than conventional machines.

It would be beneficial to provide x-ray radiography systems and methods having reduced data collection times, enhanced signal-to-noise ratios, and better x-ray source power distribution. One or more such improvements can enable new x-ray imaging and x-ray analysis applications.

Accordingly, it is desirable to provide x-ray radiography systems and methods having one or more of these improvements.

SUMMARY

It is an object of the presently disclosed subject matter to provide novel methods, systems, and computer program products for binary multiplexing x-ray radiography.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

The subject matter described herein will now be explained with reference to the accompanying drawings of which.

DETAILED DESCRIPTION

Figure 1:
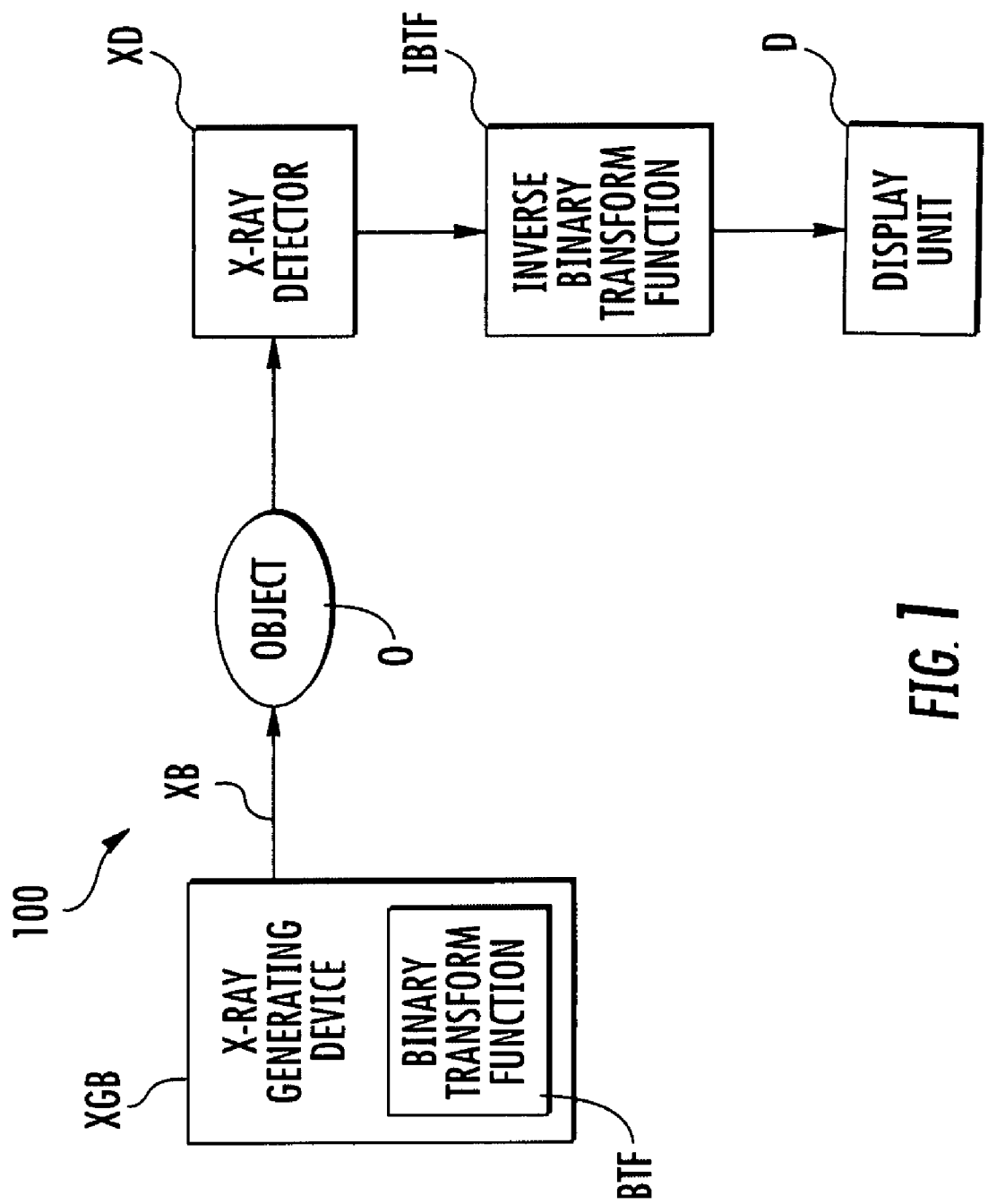
FIG. 1 is a block diagram of an exemplary BMXR system for obtaining a multi-beam image of an object according to one aspect of the subject matter described herein.

The subject matter disclosed herein is directed to a multiplexing x-ray radiographic technique that utilizes a multi-beam x-ray source, an x-ray detector, and binary transform techniques. Particularly, the radiographic techniques disclosed herein according to one aspect are referred to herein as binary multiplexing x-ray radiography (BMXR). In accordance with the BMXR techniques disclosed herein, during the data collection process, an on/off state (also referred to as the "binary state") of a multi-beam x-ray source follows the form of a predetermined binary transform. The on-off states of the x-ray source can generate x-ray beams including signals based on the predetermined binary transform. An object can be irradiated with the generated x-ray beams. After irradiation of an object, transmitted or fluorescent x-ray beams can be detected by an x-ray detector which records x-ray intensities of the multiplexing x-ray signals corresponding to the binary states of the x-ray source. The recorded x-ray intensity data can then be processed through an inverse binary transform to recover the original x-ray signals generated from each beam of the multi-beam x-ray source.

BMXR enables many new x-ray imaging and x-ray analysis applications. By using different forms of binary transforms, BMXR can reduce data collection time, enhance signal-to-noise ratio (SNR), and provide better power distribution of an x-ray source in digital radiography and fluorescence spectroscopy. By use of a multi-beam x-ray source, BMXR can allow parallel imaging/spectroscopy analysis of an object from multiple x-ray beams simultaneously using a single detector. BMXR can enhance the imaging speed in computed tomography (CT), tomosynthesis, fluoroscopy, angiography, multi-energy radiography, and x-ray fluorescence spectroscopy analysis. Suitable applications of BMXR include medical diagnostics and treatment, industrial non-destructive testing (NDT) and x-ray fluorescence (XRF) analysis, and security screening and detections.

As referred to herein, the term "nano-structured" or "nano-structure" material can designate materials including nanoparticles with particle sizes less than 100 nm, such as nanotubes (e.g. —carbon nanotubes). These types of materials have been shown to exhibit certain properties that have raised interest in a variety of applications.

As referred to herein, the term "multi-beam x-ray source" can designate devices that can simultaneously generate multiple x-ray beams. For example, the "multi-beam x-ray source" can include a field emission based multi-beam x-ray source having electron field emitters. The electron field emitters can include nano-structured materials based materials.

As referred to herein, the term "binary transform" can refer to the concept of multiplexing techniques, including Hadamard transforms and other suitable binary transforms. Generally, the binary transform can be presented by a binary transform matrix whose elements are either 1 or 0, which represents the on or off state of the signal source, respectively. Binary transforms, such as Hadamard transforms, can be applied to various kinds of applications including microscopy, optical spectroscopy, mass spectrometry, and magnetic resonance imaging (MRI).

FIG. 1 is a block diagram of an exemplary BMXR system generally designated 100 for obtaining a multi-beam image of an object according to one aspect of the subject matter described herein. Referring to FIG. 1, a binary transform function BTF can control an x-ray generating device XGD having multiple pixels to generate multiple, composite x-ray beams XB including signals based on a predetermined binary transform and configured to direct x-ray signals XS toward object O for irradiating the object. In this example, x-ray beams are being substantially projected towards object O from a single direction. Further, in this example, each of x-ray beams XB have different x-ray energy spectra. Different x-ray energy spectra can be achieved, for example, by using different anode KVp or different anode materials for the different x-ray beam pixels. In this way, BMXR can enable fast imaging in energy subtraction radiography imaging and multi-energy monochromatic imaging.

For monochromatic imaging, a system in accordance with the subject matter described herein can include a monochromator configured to generate a monochromatic x-ray beam for imaging an object. The monochromator can generate multiple monochromatic x-ray beams having either the same or different x-ray energies for monochromatic x-ray imaging.

The binary state of the signals of x-ray beams XB can be based on a predetermined binary transform. Particularly, the signals can follow the form of a predetermined binary transform matrix. The binary state of the signals of the x-ray beams can be based on a pattern of 0 and 1 elements in the predetermined binary transform matrix.

After passing through object O, x-ray beams XB can be detected by a high frame rate x-ray detector XD. X-ray detector XD can continuously capture the composite x-ray beams XB. After all or at least a portion of x-ray beams XB are collected and stored as x-ray signal data in a memory, an inverse binary transform function IBTF can apply an inverse binary transform to the stored x-ray signal data to recover the original set of generated signals.

Using the same principle of binary transform technique, BMXR in accordance with the subject matter described herein can be used to obtain multi-projection images of an object from multiple x-ray sources simultaneously using a single detector. This imaging technique can enhance the imaging speed in CT, tomosynthesis, fluoroscopy (e.g., digital fluoroscopy), angiography, and multi-energy radiography. Further, this imaging technique can lead to enhanced detection speed in industrial applications such as non-destructive testing (NDT), x-ray fluoroscopy (XRF), and diffraction.

Figure 2:
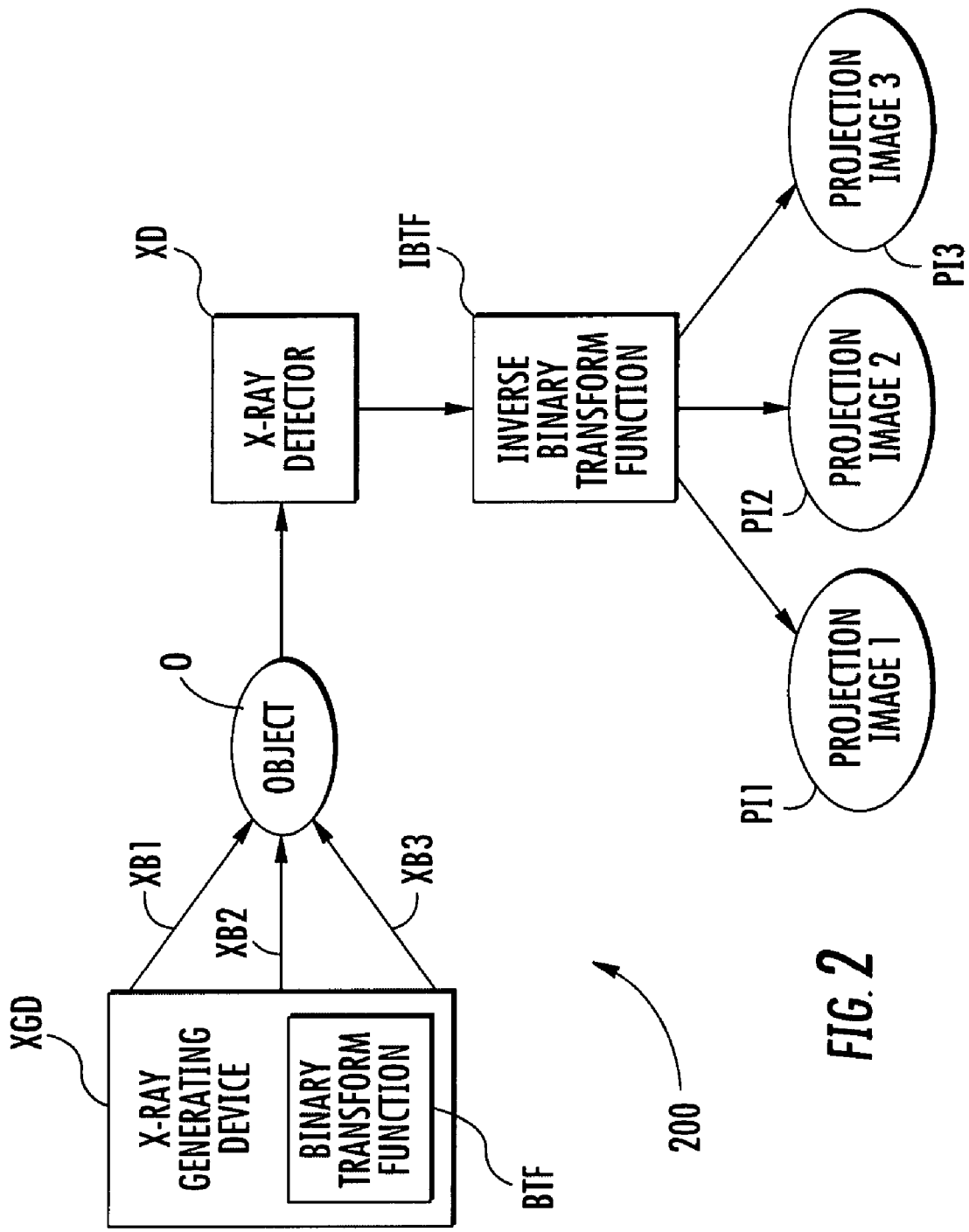
FIG. 2 is a block diagram of an exemplary BMXR system for obtaining a multi-projection image of an object according to another aspect of the subject matter described herein.

FIG. 2 is a block diagram of an exemplary BMXR system generally designated 200 for obtaining a multi-projection image of an object according to another aspect of the subject matter described herein. Referring to FIG. 2, binary transform function BTF can control multi-projection x-ray generating device XGD to generate multiple x-ray beams XB1, XB2, and XB3 under predetermined binary states for irradiating object O from different projection angles. Further, x-ray beams can be emitted simultaneously and/or in a predetermined spatial pattern.

The binary state of the signals of x-ray beams XB1, XB2, and XB3 can be based on a predetermined binary transform. Particularly, the signals can follow the form of a predetermined binary transform matrix. The binary state of the signals of the x-ray beams can be based on a pattern of 0 and 1 elements in the predetermined binary transform matrix. The following equation represents an exemplary 3×3 binary transform matrix suitable for a source projecting three x-rays beams.

$$w_{3\times 3} = \begin{pmatrix} w_{11} & w_{12} & w_{13} \\ w_{21} & w_{22} & w_{23} \\ w_{31} & w_{32} & w_{33} \end{pmatrix} \quad (1)$$

After passing through object O, x-ray beams XB can be detected by x-ray detector XD. X-ray detector XD can continuously capture the composite x-ray beams XB. In one example, x-ray detector XD can include an array or a matrix of x-ray photo diode detectors for detecting x-ray beams. In another example, x-ray detector XD can include an array or a matrix of photon counting x-ray detector elements for detecting x-ray beams. Further, for example, x-ray detector XD can be configured to record x-ray signals at a fast frame rate.

After all or at least a portion of x-ray beams XB are collected and stored as x-ray signal data in a memory, an inverse binary transform function IBTF can apply an inverse binary transform to the stored x-ray signal data to recover the original individual projection images PI1, PI2, and PI3. In this manner, each individual x-ray source can be turned on multiple times during the imaging process. Thus, data acquisition speed can be greatly enhanced due to more efficient use of the x-ray source. The more efficient use of the x-ray source can enhance the imaging speed for CT and tomosynthesis.

According to one aspect of the subject matter disclosed herein, a Hadamard multiplexing radiography is provided. The Hadamard transform is a particular example of a binary matrix transform that can be used in accordance with the present subject matter. As noted previously, any other suitable binary transform can be used. Hadamard transform includes encoding signals using a spatial modulation technique, which is inherently based on square waves (on/off state of the signal source) rather than trigonometric functions. Hadamard transform instruments can include the following: a signal source; an encoding Hadamard mask configured based on a corresponding Hadamard matrix; a detector; and a demultiplexing processor. The Hadamard transform technique superposes signals according to the Hadamard matrix. The original signals can be directly recovered from the recorded multiplexed signals by applying the inversed Hadamard transformation.

Figure 3:
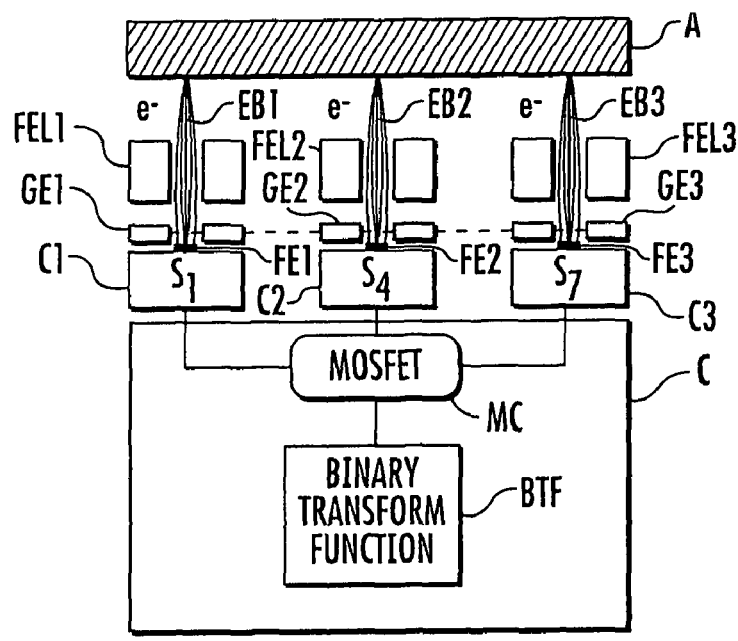
FIG. 3 is a schematic, cross-section side view of a multipixel field emission x-ray source according to an aspect of the subject matter described herein.

In accordance with the subject matter described herein, a multi-pixel x-ray source including multiple field emission x-ray sources (or pixels) and operable based on Hadamard multiplexing radiography techniques is provided. The multi-pixel x-ray source can include a multi-pixel field emission cathode with a linear array of gated electron emitting pixels. FIG. 3 is a schematic, cross-section side view of a multi-pixel field emission x-ray source generally designated 300 according to an aspect of the subject matter described herein. Referring to FIG. 3, x-ray source 300 can include a plurality of electron field emitters FE1-FE3 for emitting electrons. Electron field emitters FE1-FE3 can comprise one or more carbon nanotubes and/or other suitable electron field emission materials. Further, electron field emitters FE1-FE3 can be attached to a surface of respective cathodes C, conductive or contact line, or other suitable conductive material. Although three, linearly-arranged electron field emitters are shown in this example, a multi-pixel x-ray source in accordance with the subject matter described herein can include any suitable number and arrangement of electron field emitters.

Electron field emitters FE1-FE3 can be controlled by a suitable controller C including metal-oxide-semiconductor field-effect transmitter (MOSFET) circuitry MC and binary transform function BTF. Controller C can control voltage sources to apply voltages between electron field emitters FE1-FE3 and gate electrodes GE1-GE3, respectively, to generate respective electric fields for extracting electron from electron field emitters FE1-FE3 to thereby produce respective electron beams EB1-EB3. In particular, controller C can individually operate a plurality of MOSFETs in MOSFET circuitry MC for individually controlling field emitters FE1-FE3 to emit electrons. The drains of the MOSFETs can be connected to a corresponding one of cathodes C1-C3 for controlling electron beam emission by respective emitters FE1-FE3. The MOSFETs can be turned on and off by the individual application of high signal (e.g., 5 V) and a low signal (e.g., 0 V), respectively, to the gates of MOSFETs. When a high signal is applied to the gate of a MOSFET, a drain-to-source channel of the transistor is turned on to apply a voltage difference between a respective cathode C1-C3 and a respective gate electrode GE1-GE3. A voltage difference exceeding a threshold can generate an electric field between a respective cathode C1-C3 and a respective gate electrode GE1-GE3 such that electrons are extracted from respective electron field emitters FE1-FE3. Conversely, when a low voltage (e.g., 0 V) is applied to the gate of a MOSFET, a corresponding drain-to-source channel is turned off such that the voltage at a respective electron field emitter FE1-FE3 is electrically floating and the voltage difference between a respective cathode C1-C3 and a respective gate electrode GE1-GE3 cannot generate an electric field of sufficient strength to extract electrons from the respective electron field emitter FE1-FE3. In one example, each x-ray pixel can provide a tube current of between 0.1 and 1 mA at 40 kVp. Controller C is operable to apply voltage pulses of different frequencies to the gates of the MOSFETs. Thus, controller C can individually control the frequencies of the electron beam pulses from field emitters FE1-FE3.

Further, x-ray source 300 can include an anode A having a plurality of focus spots bombarded by a corresponding electron beam. A voltage difference can be applied between anode A and gate electrodes GE1-GE3 such respective fields are generated for accelerating electrons emitted by respective electron field emitters FE1-FE3 toward respective target structures of anode A. The target structures can produce x-ray beams having predetermined signals upon bombardment by electron beams EB1-EB3. X-ray source 300 can include focusing electrodes FEL1-FEL3 for focusing electrons extracted from respective electron field emitters FE1-FE3 on the target structures and thus reduce the size of electron beams EB1-EB3. Focusing electrodes FEL1-FEL3 can be controlled by application of voltage to focusing electrodes FEL1-FEL3 by a voltage source. The gate voltage can be varied depending on required flux. In one example, the focal spot size of each electron beam EB1-EB3 on anode A is about 200 μm.

Electron field emitters FE1-FE3 and gate electrode GE1-GE3 can be contained within a vacuum chamber with a sealed interior at about $10^{-7}$ torr pressure. The interior of the vacuum chamber can be evacuated to achieve a desired interior pressure. Electron beams EB1-EB3 can travel from the interior of the vacuum chamber to its exterior through an electron permeable portion or window. In one example, the electron permeable portion or window can be a 4″ diameter beryllium (Be) x-window. X-ray beams having distinct signals can be generated by the electron bombardment of anode A by electron beams of distinct signals. Further, anode A can be suitably shaped and/or angled such that the generated x-ray beams are transmitted toward an object from a plurality of different viewing angles.

In one aspect, binary transform function BTF can control MOSFET circuitry MC to turn off and on electron field emitters FE such that electron beams EB1-EB3 carry signals in a pattern of 0 and 1 elements in a predetermined Hadamard binary transform matrix. Corresponding x-ray beams generated by bombardment of anode A with electron beams EB1-EB3 can also carry the same signals in the pattern of 0 and 1 elements in the Hadamard binary transform matrix. Spatial modulation, or coding, of waveforms of the x-ray beam radiation generated by x-ray source 300 can be readily achieved through binary transform function BTF. The generated x-ray beams can be directed towards an object for irradiation with composite x-ray beams including signals based on the predetermined Hadamard binary transform. Anode A can be configured in a reflection mode for redirecting x-ray beams towards an object to be irradiated.

In one embodiment, an x-ray source including multi-beam pixels can include a field emission cathode with a linear array of gated carbon nanotube emitting pixels, focusing electrodes, and a molybdenum target configured in a reflection mode. These components can be housed in a vacuum chamber with a 4" diameter Be x-ray window at a base pressure of $10^{-7}$ torr. Each emitting pixel can include a 1.5 mm diameter carbon nanotube film deposited on a metal surface, a 150 μm thick dielectric spacer, and an electron extraction gate made of a tungsten grid. Further, each emitting pixel is capable of emitting 1 mA current and can be evenly spaced with a center-to-center spacing of about 1.27 cm. The anode voltage can be set at 40 kV. Gate voltage can vary depending on the flux required. Switching the x-ray beam from each pixel can be controlled by sweeping a 0-5 Volt DC pulse through a corresponding MOSFET.

The carbon nanotube film can be deposited on the metal substrate by electrophoresis. The film can have a thickness of about 1.5 mm. The film can be coated on a metal disk. All of the gate electrodes can be electrically connected. An active electrostatic focusing electrode can be placed between the gate electrode and the anode for each pixel. The electron beam can be focused into a focus area on the anode target (referred to as a focal spot) when an electrical potential is applied onto the focusing electrode. Each emitting pixel can be connected to the drain of an n-channel MOSFET, the source of which is grounded. The gate of the MOSFET can be connected to the output of a digital I/O board, which can provide a 5 V DC voltage signal.

To generate x-ray radiation, a constant DC voltage can be applied to the anode and a variable DC voltage (less than about 1 kV) can be applied to the gate electrodes. MOSFET circuitry can be used to turn on and off the emission current from the individual pixels. To activate a pixel, a 5 V signal can be applied to open the channel of a corresponding MOSFET such that the pixel formed a complete electrical circuit with the gate electrode. Electrons can be emitted from the activated pixel when the gate voltage is larger than the critical field for emission. The electrons can be accelerated by the anode voltage and bombarded on a directly opposing area on the anode to produce x-ray radiation. Other, non-activated pixels will not emit electrons because they form an open circuit. To generate a scanning x-ray beam from different origins on the target, a pulsed controlling signal with predetermined pulse width can be swept across the individuals MOSFETs. At each point, the channel can be opened to generate an electron beam from the particular pixel which produced an x-ray beam from the corresponding focal point on the target.

A subset of pixels can be activated such that they all emit electrons with either the same or different pulsing frequencies which generate x-ray beams from different focal points with either the same or different frequencies. In one example, this can be accomplished by using separate gate electrodes for the field emission pixels. Extraction voltages can be applied to the corresponding pixels with the desired pulsing frequencies to generate field emitted electrons with the desired pulsing frequencies and amplitudes. In another example, a common gate can be used for all of the electron emitting pixels. Pulsing of the electron beam can be accomplished by pulsing the activation voltage applied to the MOSFET circuit. For example, to generate a pulsed x-ray with a desired frequency f, a pulsed voltage with the same frequency f can be applied to open the corresponding MOSFET.

Figure 4A:
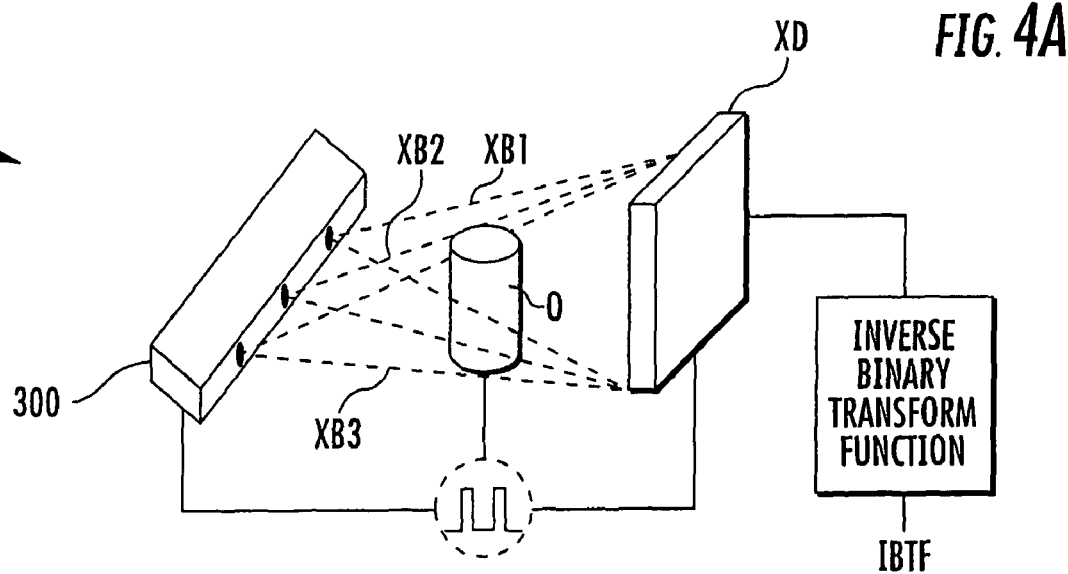
FIG. 4A is a perspective view of an x-ray imaging system including an x-ray generator device for applying binary multiplexing x-ray radiography to an object according to an embodiment of the subject matter described herein.

FIG. 4A is a perspective view of an x-ray imaging system generally designated 400 including x-ray generator device XGD for applying binary multiplexing x-ray radiography to object O according to an embodiment of the subject matter described herein. Referring to FIG. 4A, x-ray generator device XGD can include an x-ray source, such as x-ray source 300 shown in FIG. 3, for generating x-ray beams XB1-XB3 to irradiate object O. X-ray beams XB1-XB3 are shown in broken lines. Further, the beams are directed such that at least a portion of object O can be irradiated by each of the beams. X-ray beams XB1-XB3 can be generated by the bombardment of respective electron beams EB1-EB3 on anode A (shown in FIG. 3).

Object O can be placed on a sample stage in position for intercepting x-ray beams XB1-XB3, which can carry signals in a pattern of 0 and 1 elements in a predetermined Hadamard binary transform matrix. The sample stage can be rotated for rotating of object O. The signal pattern of x-ray beams XB1-XB3 can correspond to the signal pattern contained in electron beams EB1 and EB3, which is based on the predetermined Hadamard binary transform matrix. All or a portion of x-ray beams XB1-XB3 can pass through object O.

After passing through object O, x-ray beams XB1-XB3 can be detected by x-ray detector XD. X-ray detector XD can continuously capture the composite x-ray beams XB1-XB3. After all or at least a portion of x-ray beams XB1-XB3 are collected and stored as x-ray signal data in a memory, inverse binary transform function IBTF can apply an inverse binary transform to the stored x-ray signal data to recover the signals of the composite x-ray beams. In one example, x-ray detector XD can deliver a 264×264 full frame with 200 micron pixels and 16 frames per second, which is suitable for may high speed x-ray imaging applications. A display unit D can organize the recovered signals for displaying images of object O based on the recovered signals.

Figure 4B:
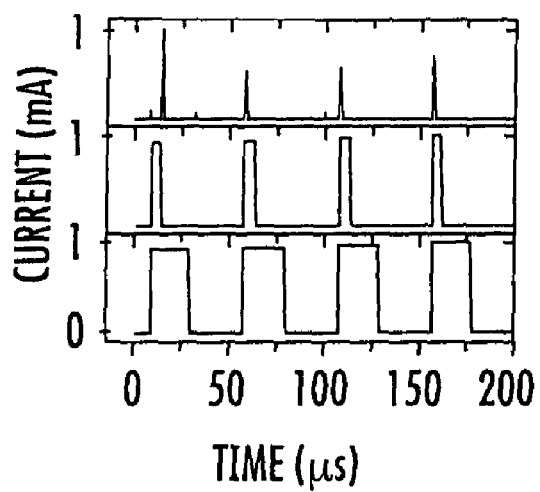
FIGS. 4B and 4C are graphs of an example of pulsed current applied to the x-ray pixels and the generated x-ray intensities over a period of time for generating pulsed x-ray radiation.
Figure 4C:
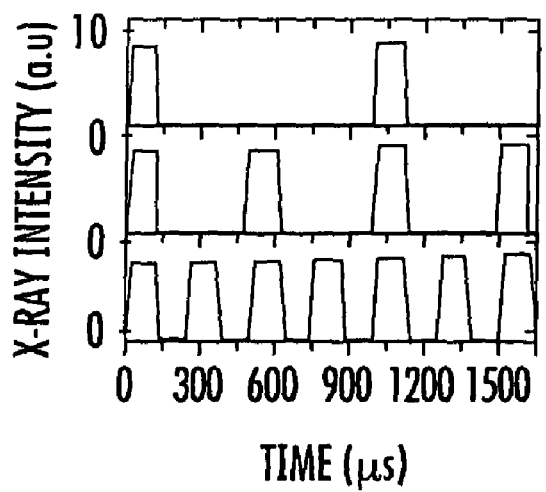

The 0 and 1 x-ray beam signals can be generated by pulsing x-ray beams XB1-XB3. The pulsed x-ray radiation can include a programmable pulse width and repetition rate. FIGS. 4B and 4C are graphs illustrating an example of pulsed current applied to the x-ray pixels and the generated x-ray intensities over a period of time for generating pulsed x-ray radiation. Referring to FIG. 4B, the x-ray tube current is shown with a variable pulse width down to 0.5 μs at a constant repetition rate of 20 kHz. Referring to FIG. 4C, x-ray pulses of variable repetition rate are shown at a constant width 150 μs acquired from a Si-PIN photodiode detector.

In Hadamard multiplexing, the multiplexed signals are generated from original signals weighted by 0 and 1. Assuming the original signals have the form $X=[x_1\ x_2\ \ldots\ x_{N-1}\ x_N]^T$, the multiplexed signals $Y=[y_1\ y_2\ \ldots\ y_{N-1}\ y_N]^T$ are in general related to the original signals by the linear transform Y=SX. For a Hadamard transform, the S-matrices consist of only 1s and 0s, which correspond to the on/off state of the signal source. The inverse of such a matrix is obtained by replacing the elements in the matrix by −1s and scaling by 2/(n+1).

As an example for the S matrix of order N=3, the convolution process can be expressed succinctly in the matrix notation by the following equation:

$$\begin{bmatrix} y_1 \\ y_2 \\ y_3 \end{bmatrix} = \begin{bmatrix} 1 & 1 & 0 \\ 1 & 0 & 1 \\ 0 & 1 & 1 \end{bmatrix} \begin{bmatrix} x_1 \\ x_2 \\ x_3 \end{bmatrix} = \begin{bmatrix} x_1 + x_2 \\ x_1 + x_3 \\ x_2 + x_3 \end{bmatrix} \quad (2)$$

The original signals can be recovered from the multiplexed signals by applying the inversed Hadamard matrix to both sides of equation (2), as illustrated by the following equation (3):

$$\begin{bmatrix} x_1 \\ x_2 \\ x_3 \end{bmatrix} = \frac{2}{N(=3)+1} \begin{bmatrix} 1 & 1 & -1 \\ 1 & -1 & 1 \\ -1 & 1 & 1 \end{bmatrix} \begin{bmatrix} y_1 \\ y_2 \\ y_3 \end{bmatrix} \quad (3)$$

Figure 5A:
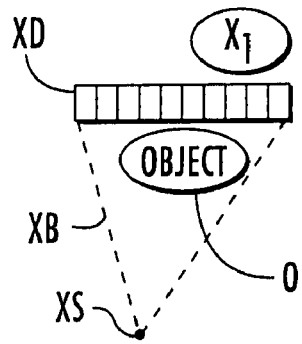
FIGS. 5A-5C are schematic diagrams of a conventional scanning sequential imaging system that is imaging an object in sequence from different projection angles.
Figure 5B:
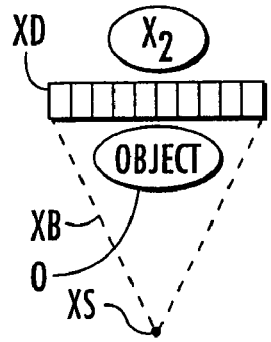
Figure 5C:
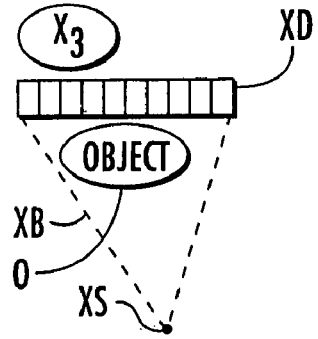

For Hadamard multiplexing radiography of order N=3, an exemplary comparison of conventional imaging and data processing procedures with procedures Hadamard techniques according to the subject matter described herein are described with respect to FIGS. 5A-5C and 6A-6C. FIGS. 5A-5C illustrate conventional scanning sequential imaging of object O by a x-ray detector XD and x-ray source XS at times t1-t3, respectively. Referring to FIGS. 5A-5C, projection images of object O are collected sequentially at times t1-t3 in the time domain by irradiating object O with x-ray beam XB. Object O is irradiated by x-ray beam XB from different projection angles by x-ray source XS. X-ray detector XD detects a portion of x-ray beam XB passing through object O. The total imaging time is $3\Delta t$, assuming exposure time $\Delta t$ for each projection image.

Figure 6A:
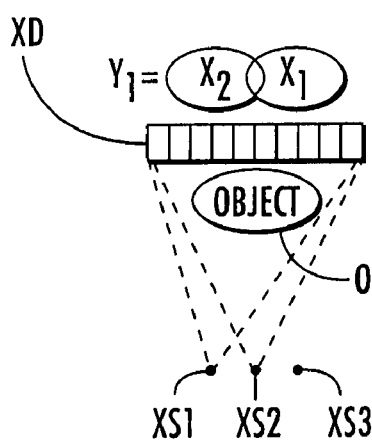
FIGS. 6A-6C are schematic diagrams of an exemplary BMXR system that is imaging an object in accordance with the subject matter described herein.
Figure 6B:
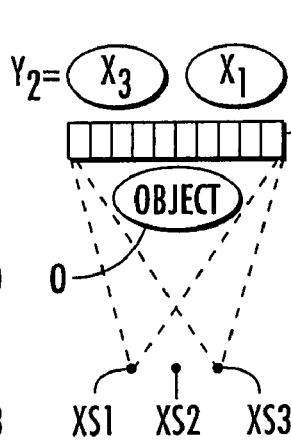
Figure 6C:
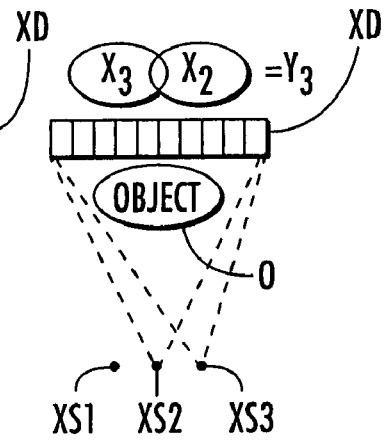

For the Hadamard multiplexing imaging example shown in FIGS. 6A-6C, the total number of exposures is 3, the same as in the FIGS. 5A-5C example. However, in the example of FIGS. 6A-6C, only two of x-ray sources XS1, XS2, and XS3 are turned on simultaneously for each exposure of object to x-ray beams XB1, XB2, and XB3 according to the 1/0 (on/off) pattern of the Hadamard matrix shown in equation (2) above. Since each individual x-ray source XS1-XS3 is turned on twice during the three exposures to keep the dose constant, the exposure time for each frame can be reduced to $\Delta t/2$. The overall exposure time for the FIGS. 6A-6C example is $1.5\Delta t$ compared to $3\Delta t$ for sequential imaging as in the FIGS. 5A-5C example. In general for Hadamard multiplexing radiography of order N, the data acquisition rate can be improved by a factor of $(N+1)/2$. Considering the fact that the order of 1000 images (N~1000) are required for each gantry rotation in CT scanning, a large gain is provided in imaging speed in techniques according to the subject matter described herein. On the other hand, since each x-ray source is turned on $(N+1)/2$ times during the entire data collection process, thus keeping the total exposure time fixed, the maximum workload of the x-ray tube needed to achieve the same x-ray dose for each image can be reduced by a factor of $(N+1)/2$.

Figure 7:
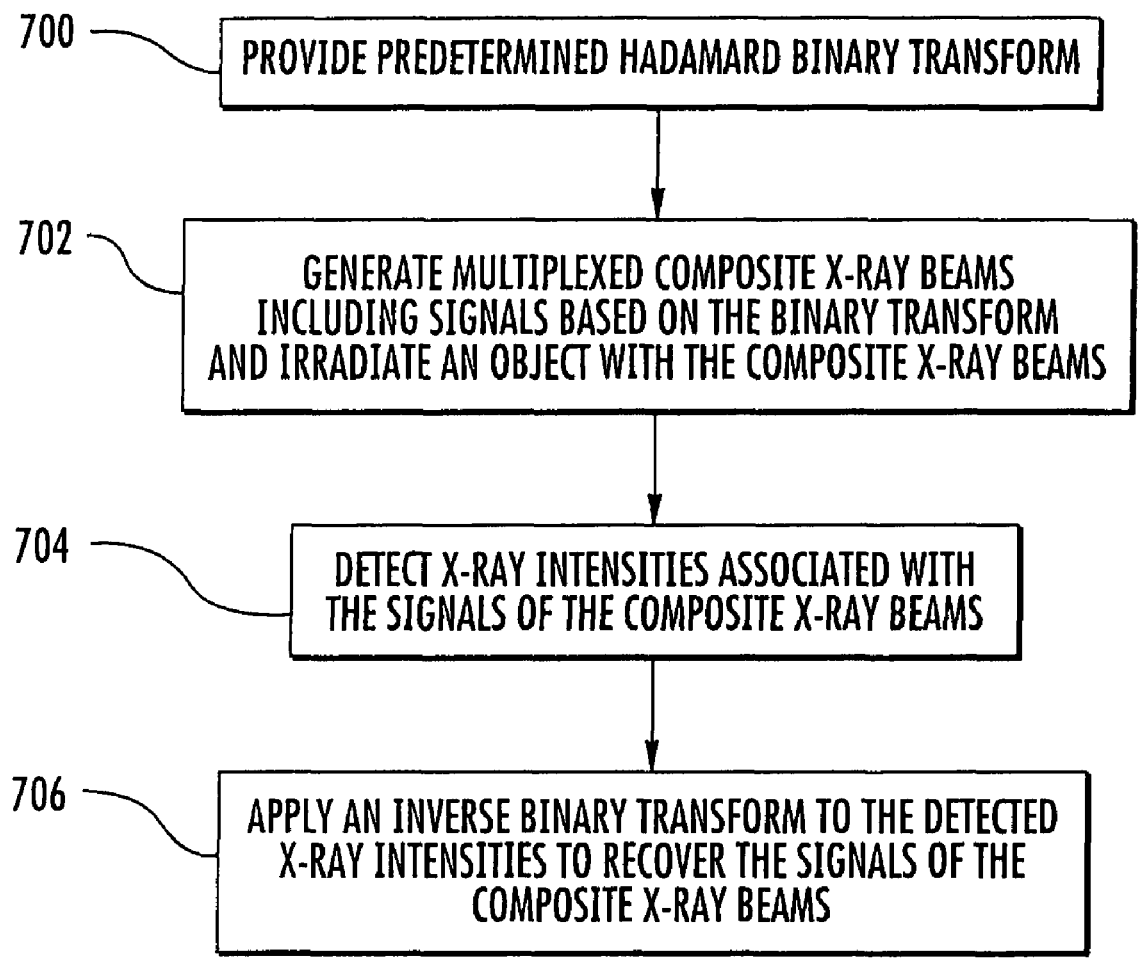
FIG. 7 is a flow chart of an exemplary process of binary multiplexing x-ray radiography according to an embodiment of the subject matter described herein.

FIG. 7 is a flow chart illustrating an exemplary process of binary multiplexing x-ray radiography according to an embodiment of the subject matter described herein. In this example, the process is based on a Hadamard binary transform, although any other suitable binary transform may be utilized. Referring to FIG. 7, a predetermined Hadamard binary transform can be provided (block 700). For example, the binary transform can be stored in a memory. The Hadamard binary transform can be based on a Hadamard matrix such as the matrix represented by the following equation (4):

$$S_N = \begin{pmatrix} s_{11} & \cdots & s_{1N} \\ \cdots & \cdots & \cdots \\ s_{N1} & \cdots & s_{NN} \end{pmatrix} \quad (4)$$

In this example, the multiplexing radiography is order N=7, although any other order may be used based on the number of x-ray sources or pixels.

Figure 8:
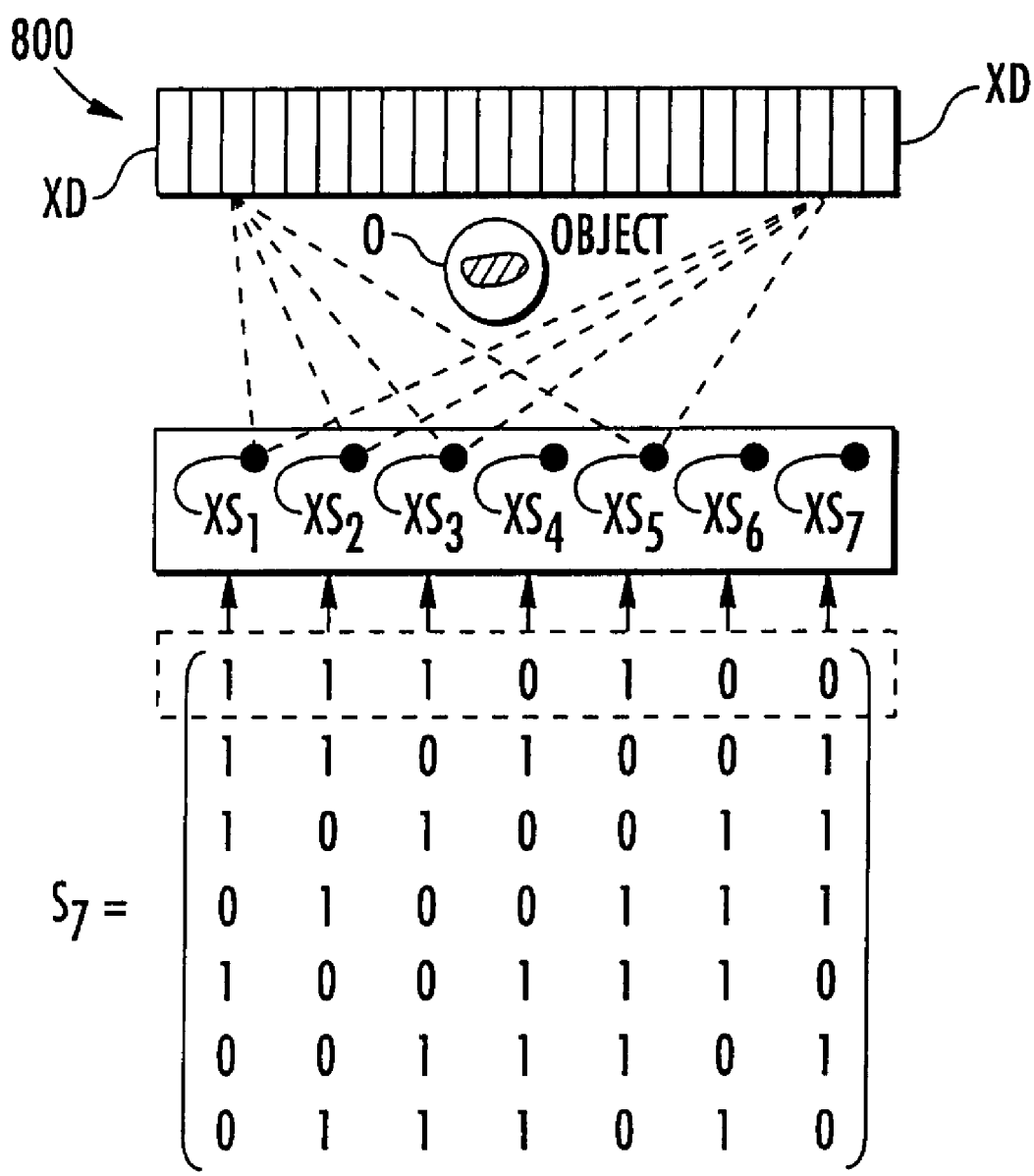
FIG. 8 is a schematic diagram of an exemplary BMXR system operable to generate multiplexed composite x-ray beams including signals based on the predetermined Hadamard binary transform and irradiate an object with the composite x-ray beams according to an embodiment of the subject matter described herein.
Figure 11A:
FIGS. 11A-11G are of the computer board used to obtain the image shown in FIG. 10.
Figure 11B:
Figure 11C:
Figure 11D:
Figure 11E:
Figure 11F:
Figure 11G:
Figure 12A:
FIGS. 12A-12G are individual projection images of the computer board from different viewing angles obtained by demultiplexing the multiplexed x-ray images shown in FIG. 11.
Figure 12B:
Figure 12C:
Figure 12D:
Figure 12E:
Figure 12F:
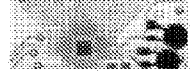
Figure 12G:

In block 702, a binary transform function can generate multiplexed composite x-ray beams including signals based on the predetermined Hadamard binary transform and irradiate an object with the composite x-ray beams. For example, FIG. 8 is a schematic diagram illustrating an exemplary BMXR system generally designated 800 operable to generate multiplexed composite x-ray beams including signals based on the predetermined Hadamard binary transform and irradiate an object with the composite x-ray beams according to an embodiment of the subject matter described herein. Referring to FIG. 8, system 800 includes a plurality of x-ray sources (or pixels) XS1-XS7 configured to produce x-ray beams including signals based on a predetermined binary transform such as a Hadamard transform.

X-ray sources XS1-XS7 are individually addressable x-ray pixels. Each field emission pixel can be comprised of a gated carbon nanotube field emission cathode, a tungsten mesh extraction gate, and an electrostatic focusing lens. The cathode can be a random carbon nanotube composite film deposited on a metal substrate by electrophoresis. A MOSFET-based electronic circuit can control the on/off pattern of the x-ray sources.

The x-ray beams generated by x-ray sources XS1-XS7 can be controlled by a binary transform function to include signals based on the Hadamard binary transform matrix $S_7$. X-ray beams of x-ray sources XS1-XS7 can be applied to object O in sequence until the composite x-ray beams have been applied. Object O can be positioned on a sample stage. The first application of x-ray beam signals (shown in FIG. 8) include turning on x-ray sources XS1, XS2, XS3, and XS5 in accordance with the Hadamard binary transform matrix $S_7$.

As shown in the Hadamard binary transform matrix $S_7$ of FIG. 8, the 1s and 0s in each row of the Hadamard matrix are used to control the on (1) and off (0) state of a corresponding x-ray source XS1-XS7. To generate a multiplexing x-ray beam from multiple origins on object O, a controlling signal with a predetermined signal pattern and pulse width was swept across a control circuit (such as a MOSFET control circuit). A total number of N=7 multiplexed images can be acquired based on the following signal sequences: (1110100); (1101001); (1010011); (0100111); (1001110); (0011101); and (0111010). The seven multiplexed images can be collected and stored in a memory.

In the first application, x-ray sources XS4, XS6, and XS7 are turned off. The sequence of x-ray beams includes six more applications x-ray beam signals. The control of x-ray beam sources XS1-XS7 to apply the applications is shown in the Hadamard binary transform matrix $S_7$. The generation of each multiplexed image is based on the corresponding row of the Hadamard matrix. The on/off state of each x-ray source is determined by the 1/0 matrix element in that row.

Referring again to FIG. 7, x-ray intensities associated with the signals of the composite x-ray beams can be detected (block 704). For example, x-ray detector XD shown in FIG. 8 can detect the x-ray intensities associated with the signals of the composite x-ray beams generated by x-ray sources XS1-XS7. X-ray detector XD can be a single flat panel x-ray detector. The x-ray intensities comprise multiplexed x-ray images.

In block 706, an inverse binary transform can be applied to the detected x-ray intensities associated with the signals of the composite x-ray beams to recover the signals of the composite x-ray beams. For example, an inverse binary transform function can apply an inverse binary transform to the detected x-ray intensities associated with the signals of the composite x-ray beams to recover the signals of the composite x-ray beams. In one example, after a complete set of multiplexed images are collected, a demultiplexing algorithm based on a corresponding inversed Hadamard transform matrix can be applied to the complete set of multiplex images to recover the original projection images.

Figure 9:
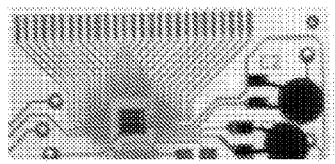
FIG. 9 is a reference image of the computer circuit acquired using a conventional sequential imaging technique.
Figure 10:
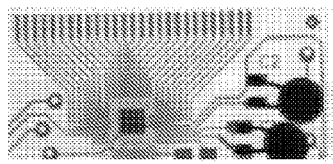
FIG. 10 is a multiplexing image of the circuit board acquired in accordance with the subject matter described herein.

In one experiment, images of a computer circuit were acquired using conventional techniques and techniques in accordance with the subject matter described herein. FIG. 9 is a reference image of the computer circuit acquired under the same imaging conditions (kV, mAs, and imaging configuration) using a conventional sequential imaging technique. For comparison, FIG. 10 is a multiplexing image of the circuit board acquired in accordance with the subject matter described herein. The quality of the images shown in FIGS. 9 and 10 is visually negligible (3% based on the quantitative contrast calculation). In terms of imaging speed, a factor of 4 increase in the speed has been achieved using Hadamard imaging techniques in accordance with the subject matter described herein.

FIGS. 11A-11G are multiplexed x-ray images of the computer board used to obtain the image shown in FIG. 10. A demultiplexing algorithm based on inversed Hadamard transform techniques in accordance with the subject matter described herein was applied to demultiplex the multiplexed images of FIGS. 11A-11G. FIGS. 12A-12G are individual projection images of the computer board from different viewing angles. The image of FIG. 10 is one of the demultiplexed images of the circuit board.

Figure 13:
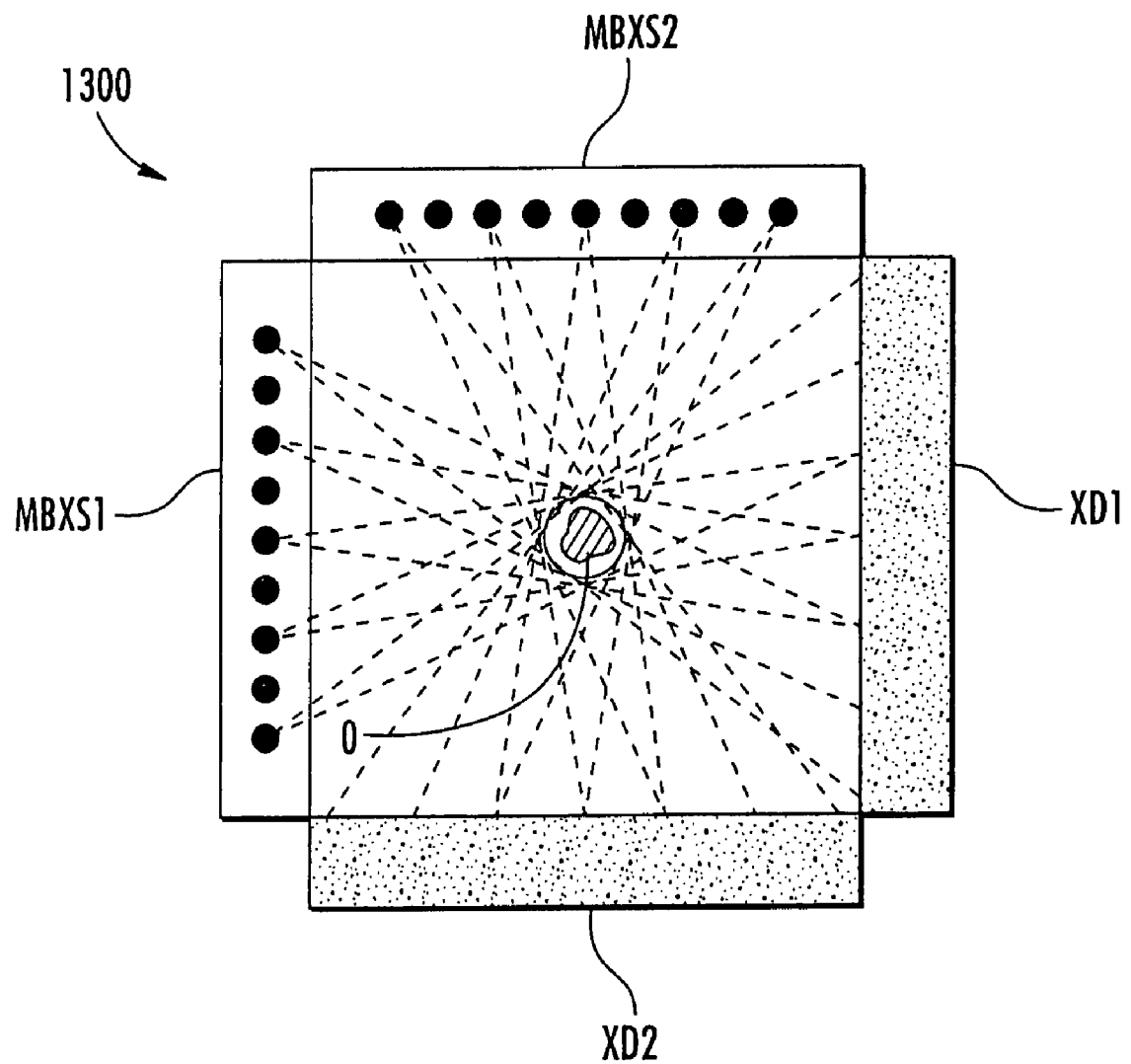
FIG. 13 is a schematic diagram of an exemplary CT imaging system having multi-beam field emission pixels according to an embodiment of the subject matter described herein.

Systems and methods in accordance with the subject matter described herein may also be included in a CT imaging system having multi-beam field emission pixels. FIG. 13 is a schematic diagram of an exemplary CT imaging system generally designated 1300 having multi-beam field emission pixels according to an embodiment of the subject matter described herein. Referring to FIG. 13, system 1300 can include multi-beam x-ray sources MBXS1 and MBXS2 that each include multiple pixels configured for directing x-ray beams at object O. The pixels of x-ray sources MBXS1 and MBXS2 can be controlled to turn on and turn off in a signaling pattern based on a predetermined binary transform. Object O can be positioned for irradiation by the x-ray beams. X-ray detectors XD1 and XD2 can be area x-ray detectors configured to detect x-ray beams from x-ray sources MBXS1 and MBXS2, respectively. An inverse binary transform function can receive detected x-ray intensity data associated with the signals and apply an inverse binary transform to the detected x-ray intensities associated with the signals of the composite x-ray beams to recover the signals of the composite x-ray beams. Images can be generated based on the recovered signals.

Several different factors can contribute to multiplexing imaging artifacts. Some artifacts, such the artifact introduced by insufficient data sampling, can be difficult to resolve due to the limitation of current x-ray detector technology. In the case of imaging in accordance with the subject matter described herein, the imaging artifact is simply from the intensity fluctuation of the x-ray signals/field emission current. In order to minimize the x-ray intensity fluctuation, either hardware-based or software-based feedback circuitry can be applied to stabilize the field emission current from a carbon nanotube pixel.

For scattered x-ray radiation, the deleterious effects of scattering on imaging quality in x-ray imaging have been well documented. Compared with sequential imaging, the multiplexing imaging generally introduced more scattering components due to the fact that multiple x-ray signals were turned on simultaneously during the imaging process. It can also be shown that the scattered radiations in Hadamard imaging are also multiplexed in the same fashion as their primary counterparts. The demultiplexing process will also demultiplex the scattered radiation from each x-ray pixel to prevent the severe degradation of imaging contrast and accumulation of background noise. An anti-scattering device can be configured to minimize scattered x-ray signals collected by an x-ray detector.

If the x-ray exposure dose for each individual x-ray beam signal is fixed, the BMXR methods and systems in accordance with the subject matter described herein can be utilized such that the overall data collection time can be dramatically reduced in comparison to conventional techniques. In conventional x-ray radiography, there is only one signal source turned on at a given time. Multiple x-ray signals have to be collected on after the other, which is referred to as a sequential data collection method. This method can greatly limit the overall imaging speed. In BMXR in accordance with the subject matter described herein, multiple x-ray signals can be collected simultaneously. This parallel data collection mechanism can significantly reduce the overall data collection time in comparison to conventional techniques.

If the total exposure time is fixed, the BMXR methods and systems in accordance with the subject matter described herein can be utilized to improve the signal-to-noise ratio of the signal in comparison to conventional techniques. The increase of signal-to-noise ratio in x-ray imaging or analysis is often limited by the maximum x-ray flux, or equivalently the maximum output power, of the x-ray source due to the finite exposure time. The maximum output power is generally limited by the finite heat dissipation rate of the target and small focal spot size. The binary multiplexing techniques as described herein can increase the signal-to-noise ratio by simultaneously turning on multiple x-ray signal channels during the imaging process. This technique can enhance the signal-to-noise ratio due to the fact that the actual exposure time used for taking each signal is greatly extended without increasing the overall exposure time.

If the exposure does for each individual signal and total exposure time are fixed, the BMXR methods and systems in accordance with the subject matter described herein can provide better power distribution of the x-ray source in comparison to conventional techniques. In this case, compared with the conventional serial data collection method, the available exposure time for each individual source is much longer since each of them will be turned on multiple times. The demanded tube current for each x-ray source can be greatly reduced based on the number of times it can be turned on during the data collection process. Since less tube current is required, both cathode and anode life times and overall x-ray tube life time can be improved using the BMXR methods and systems described herein.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of binary multiplexing x-ray radiography, the method comprising:
irradiating an object from a plurality of different locations with N composite x-ray beams including signals from N different x-ray sources based on a predetermined binary transform in which each of the different x-ray sources is turned on at least (N+1)/2 times;
detecting x-ray intensities associated with the signals of the composite x-ray beams that have passed through the object; and applying an inverse binary transform to the detected x-ray intensities associated with the signals of the composite x-ray beams to recover the signals from the different x-ray sources.

2. The method of claim 1 wherein irradiating an object comprises irradiating the object with the composite x-ray beams generated by a plurality of x-ray sources.

3. The method of claim 1 wherein the x-ray sources comprise multi beam field emission x-ray sources.

4. The method of claim 1 wherein irradiating an object comprises irradiating the object with a predetermined pattern of the composite x-ray beams.

5. The method of claim 1 wherein irradiating an object comprises irradiating the object with composite x-ray beams including signals based on a predetermined Hadamard binary transform.

6. The method of claim 1 wherein irradiating the object with composite x-ray beams comprises irradiating the object with a plurality of monochromatic x-ray beams.

7. The method of claim 1 irradiating the object with a plurality of x-ray beams having different ray energies.

8. The method of claim 1 wherein detecting x-ray intensities comprises detecting the x-ray intensities with an one dimensional array or two dimension array of x-ray detectors.

9. The method of claim 8 wherein the x-ray detector is configured to record the x-ray intensities associated with the signals of the composite x-ray beams at a fast frame rate.

10. A binary multiplexing x-ray radiography system comprising:
a plurality of x-ray sources configured to irradiate an object from a plurality of different locations with N composite x-ray beams including signals from N individual x-ray beams based on a predetermined binary transform in which each of the individual x-ray beams is turned on at least (N+1)/2 times;
an x-ray detector configured to detect x-ray intensities associated with the signals of the composite x-ray beams that have passed through the object; and
an inverse binary transform function processor configured to apply an inverse binary transform to the detected x-ray intensities associated with the signals of the composite x-ray beams to recover the signals from individual x-ray beams.

11. The system of claim 10 wherein the x-ray sources comprise a plurality of field emission x-ray sources.

12. The system of claim 10 wherein the x-ray sources are configured to irradiate the object with a predetermined pattern of the composite x-ray beams.

13. The system of claim 10 wherein the x-ray sources are configured to irradiate the object with composite x-ray beams including signals based on a predetermined Hadamard binary transform.

14. The system of claim 10 wherein the plurality of x-ray sources are configured to irradiate the object with a plurality of monochromatic x-ray beams.

15. The system of claim 10 wherein irradiating the object with a plurality of x-ray beams with different energies.

16. The system of claim 10 wherein the x-ray detector comprises an array of one dimensional or two dimensional detector elements.

17. The system of claim 10 wherein the x-ray detector is configured to record the x-ray intensities associated with the signals of the composite x-ray beams at a fast frame rate.

18. A computer program product comprising computer-executable instructions embodied in a non-transitory computer-readable medium for directing a computer to perform steps comprising:
irradiating an object from a plurality of different locations with N composite x-ray beams including N individual signals based on a predetermined binary transform in which each of the individual signals is turned on at least (N+1)/2 times;
detecting x-ray intensities associated with the signals of the composite x-ray beams that have passed through the object; and
applying an inverse binary transform to the detected x-ray intensities associated with the signals of the composite x-ray beams to recover the signals from individual x-ray beams.

19. A binary multiplexing computed tomography x-ray imaging system comprising:
a plurality of x-ray sources configured to irradiate an object with N composite x-ray beams including signals from N individual x-ray beams based on a predetermined binary transform in which each of the individual x-ray beams is turned on at least (N+1)/2 times;
an x-ray detector configured to detect x-ray intensities associated with the signals of the composite x-ray beams;
an object stage positioned between the plurality of x-ray sources and the x-ray detector;
an electronic controller and a first computer program that enable the system to collect a sequence of composite images of the object corresponding to the x-ray intensities;
a second computer program that applies an inverse binary transform to the composite images to obtain the projection images of the object from the individual x-ray beams; and
an image reconstruction program to generate computed tomography images of the object.

20. The device of claim 19 wherein the binary transform is a Hadamard binary transform.

21. The device of claim 19 comprising an anti-scattering device configured to minimize scattered x-ray signals collected by the x-ray detector.

22. The device of claim 19 comprising a third computer program configured to analyze each composite x-ray image and configured to remove scattered x-ray intensities from the multiple x-ray beams based on an algorithm.

23. The device of claim 19 wherein the multiple x-ray emitting pixels are one of enclosed in one vacuum enclosure, enclosed in several vacuum enclosures wherein each vacuum enclosure contains a plurality of x-ray pixels, and enclosed in several vacuum enclosures wherein each vacuum enclosure encloses a single x-ray pixel.

24. The device of claim 19 wherein the x-ray source is an electron field emission multi-pixel x-ray source.

* * * * *

UNITED STATES PATENT AND TRADEMARK OFFICE
CERTIFICATE OF CORRECTION

| | | |
|---|---|---|
| PATENT NO. | : 8,189,893 B2 | |
| APPLICATION NO. | : 11/804897 | |
| DATED | : May 29, 2012 | |
| INVENTOR(S) | : Zhang et al. | |

It is certified that error appears in the above-identified patent and that said Letters Patent is hereby corrected as shown below:

At Column 1, Line 14, under the heading "GOVERNMENT INTEREST":

Please replace:

"This work was supported at least in part by a grant from the National Institute of Health and the National Institute of Biomedical Imaging and Bioengineering (NIH-NIBIB) (Grant No. 4-R33-EB004204-02), and a grant from the National Cancer Institute (NCI) (Grant No. U54CA119343). Thus, the U.S. Government may have certain rights in the presently disclosed subject matter."

With the following paragraph:

-- This invention was made with government support under Grant Nos. 4-R33-EB004204-02 and U54CA119343 awarded by the National Institute of Health and the National Institute of Biomedical Imaging and Bioengineering, and the National Cancer Institute. The government has certain rights in the invention. --

Signed and Sealed this
Twenty-fourth Day of July, 2012

David J. Kappos
*Director of the United States Patent and Trademark Office*